United States Patent [19]

Debono

[11] 4,293,491

[45] Oct. 6, 1981

[54] DERIVATIVES OF A-30912H NUCLEUS

[75] Inventor: Manuel Debono, Indianapolis, Ind.

[73] Assignee: Eli Lilly and Company, Indianapolis, Ind.

[21] Appl. No.: 182,248

[22] Filed: Aug. 25, 1980

Related U.S. Application Data

[63] Continuation-in-part of Ser. No. 103,147, Dec. 13, 1979, abandoned.

[51] Int. Cl.³ .......................................... C07C 103/52
[52] U.S. Cl. ............................................. 260/112.5 R
[58] Field of Search ................................ 260/112.5 R

[56]   References Cited

U.S. PATENT DOCUMENTS

| | | | |
|---|---|---|---|
| 3,150,059 | 9/1964 | Kleizschmidt | 260/112.5 R |
| 3,978,210 | 8/1976 | Mizuno et al. | 260/112.5 R |
| 4,024,245 | 5/1977 | Hoehn et al. | 260/112.5 R |
| 4,024,246 | 5/1977 | Higgens et al. | 260/112.5 R |
| 4,050,989 | 9/1977 | Kuwana et al. | 260/112.5 R |
| 4,173,629 | 11/1979 | Dreyfuss et al. | 260/112.5 R |

FOREIGN PATENT DOCUMENTS

| | | | |
|---|---|---|---|
| 568386 | 4/1972 | Belgium | 260/112.5 R |
| 834289 | 10/1974 | Belgium | 260/112.5 R |
| 859067 | 2/1977 | Belgium | 260/112.5 R |
| 866095 | 4/1977 | Belgium | 260/112.5 R |
| 851310 | 8/1977 | Belgium | 260/112.5 R |

OTHER PUBLICATIONS

Tetrahedron Letters No. 46, pp. 4147–4150, 1976.
Helvetica Chimica Acta–vol. 62, Fasc. 4 (1979) 1252–1266.
The Journal of Antibiotics 1976, 380–389, vol 29, No. 4.
The Journal of Antibiotics 1976, 1268–1274 vol. 29, No. 12.
The Journal of Antibiotics vol. 29, No. 12 1275–1280, 1976.
Helvetica Chimica Acta, vol. 57, Fasc. 8 (1974) 2459–2477.
The Journal of Antibiotics vol. 29, No. 12, 1339–1340, 1976.
Agr. Biolg. Chem., 37 (112), 2455–2463, 1973.
Agr. Biol. Chem., 37 (12), 2709–2717, 1973.
Agr. Biol. Chem., 38 (3), 521–529, 1974.
Agr. Biol. Chem. 38 (10), 1767–1777 (1974).
The Journal of Biochemistry, vol. 56, No. 4, 1964. 335–343.
The Journal of Antibiotics vol. 31, No. 4, 373–374, (1978).
The Journal of Antibiotics (1975) 764–769, vol. 28, No. 10.

*Primary Examiner*—Delbert R. Phillips
*Attorney, Agent, or Firm*—Nancy J. Harrison; Arthur R. Whale

[57]   ABSTRACT

Compounds of the formula

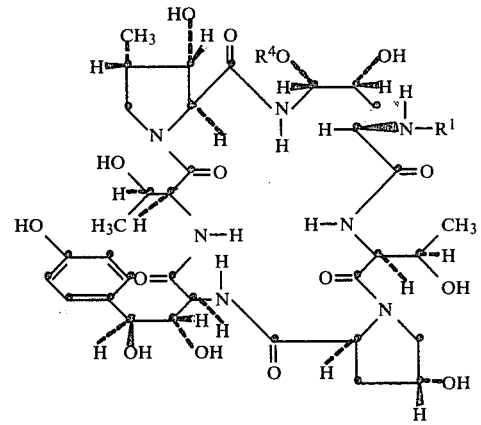

wherein $R^4$ is $C_1$–$C_6$ alkyl and $R^1$ is an N-alkanoyl amino acyl group of the formula

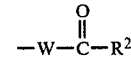

wherein:
W is a divalent aminoacyl radical of the formula

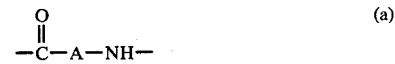

wherein A is $C_1$–$C_{10}$ alkylene or $C_5$–$C_6$ cycloalkylene;

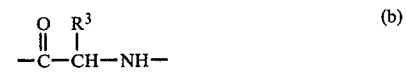

wherein $R^3$ is hydroxymethyl, hydroxyethyl, mercaptomethyl, mercaptoethyl, methylthioethyl, 2-thienyl, 3-indolemethyl, phenyl, benzyl, or substituted phenyl or substituted benzyl in which the benzene ring thereof is substituted with chloro, bromo, iodo, nitro, $C_1$–$C_3$ alkyl, hydroxy, $C_1$–$C_3$ alkylthio, carbamyl, or $C_1$–$C_3$ alkylcarbamyl;

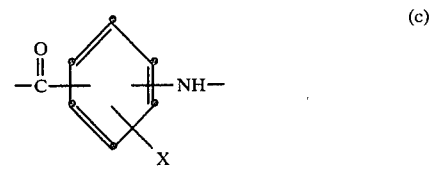

wherein X is hydrogen, chloro, bromo, iodo, nitro, $C_1$–$C_3$ alkyl, hydroxy, $C_1$–$C_3$ alkoxy, mercapto, $C_1$–$C_3$ alkylthio, carbamyl, or $C_1$–$C_3$ alkylcarbamyl;

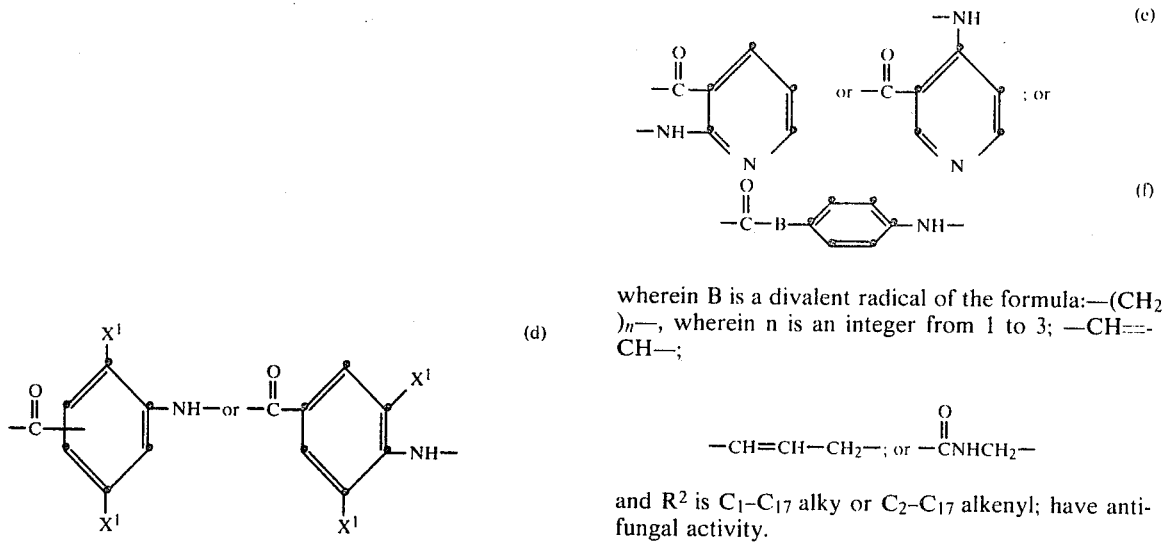
(d) wherein $X^1$ is chloro, bromo, or iodo;
wherein B is a divalent radical of the formula: $-(CH_2)_n-$, wherein n is an integer from 1 to 3; $-CH=CH-$;
$-CH=CH-CH_2-$; or $-\overset{O}{\underset{\|}{C}}NHCH_2-$
and $R^2$ is $C_1-C_{17}$ alky or $C_2-C_{17}$ alkenyl; have antifungal activity.
25 Claims, No Drawings

DERIVATIVES OF A-30912H NUCLEUS

CROSS-REFERENCE TO RELATED APPLICATION

This application is a continuation-in-part of application Ser. No. 103,147, filed Dec. 13, 1979, now abandoned.

BACKGROUND OF THE INVENTION

This invention relates to novel semisynthetic antifungal compounds which are prepared by the acylation of the cyclic peptide nucleus produced by the enzymatic deacylation of antibiotic A30912 factor H or of a alkyl ether homolog thereof.

Antibiotic A-30912 factor H is an antifungal cyclic peptide having the formula:

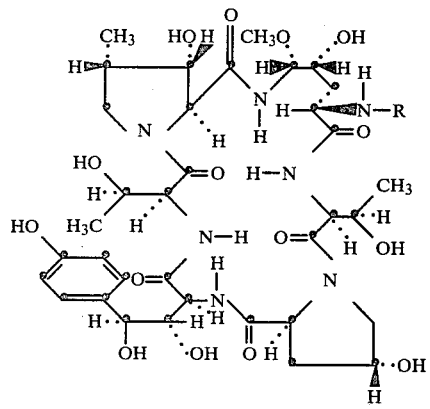

wherein R is the linoleoyl group

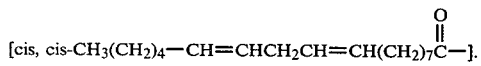

Throughout this application, the cyclic peptide formulas, such as formula I, assume that the amino acids represented are in the L-configuration. The factor is isolated from the A30912 complex which contains other factors arbitrarily designated factors A, B, C, D, E, F, and G. The A-30912 complex and the individual factors A through G are disclosed by M. Hoehn and K. Michel in U.S. Pat. No. 4,024,245. Antibiotic A-30912 factor A is identical to antibiotic A-22802 which is described by C. Higgins and K. Michel in U.S. Pat. No. 4,024,246. Factor H is a later-discovered antibiotic A-30912 factor, and it is disclosed in the copending application of Karl H. Michel entitled "ANTIBIOTIC A-30912 FACTOR H," Ser. No. 117,739, filed Feb. 1, 1980, which is a continuation-in-part of application Ser. No. 46,875, filed June 8, 1979, (now abandoned), the entire disclosure of which is incorporated herein by reference.

Antibiotic A-30912 factor H is prepared by fermentation using one of several different organisms, namely: (a) *Aspergillus rugulosus* NRRL 8113 (see U.S. Pat. No. 4,024,245), or (b) *Aspergillus nidulans* var. *roseus* NRRL 11440 (see co-pending application of L. Boeck and R. Kastner, METHOD OF PRODUCING THE A-30912 ANTIBIOTICS, Ser. No. 126,078, filed Mar. 3, 1980, which is a continuation-in-part of application Ser. No. 46,744, filed June 8, 1979, (now abandoned), the entire disclosure of which is incorporated herein by reference.)

A subculture of *A. nidulans* var. *roseus* has been deposited and made a part of the permanent culture collection of the Northern Regional Research Laboratory, U.S. Department of Agriculture, Agricultural Research Service, Peoria, Ill. 61604, from which it is available to the public under the number NRRL 11440.

When a strain of *A nidulans* var. *roseus* NRRL 11440 is used to produce A-30912 factor H, a complex of factors is obtained which for convenience is called the A-42355 antibiotic complex. A-30912 factor A is the major factor of the A-42355 antibiotic complex, while factors B, D and H are minor factors. Examples 6, 7, and 8 herein, illustrate the preparation of the A-42355 complex and the isolation and purification of A-30912 factor H therefrom.

In the antibiotic A-30912 factor H molecule (Formula I), the linoleoyl side chain (R) is attached at the cyclic peptide nucleus at the α-amino group of the methoxyhydroxyornithine residue. Surprisingly, it has been found that the linoleoyl side chain can be cleaved from the nucleus by an enzyme without affecting the chemical integrity of the nucleus. The enzyme employed to effect the deacylation reaction is produced by a microorganism of the family Actinoplanaceae, preferably the microorganism *Actinoplanes utahensis* NRRL 12052, or a variant thereof. To accomplish deacylation, antibiotic A30912 factor H is added to a culture of the microorganism and the culture is allowed to incubate with the substrate until the deacylation is substantially complete. The cyclic nucleus thereby obtained is separated from the fermentation broth by methods known in the art. Unlike antibiotic A-30912 factor H, the cyclic nucleus (lacking the linoleoyl side chain) is substantially devoid of antifungal activity.

The cyclic nucleus afforded by the aforedescribed enzymatic deacylation of antibiotic A-30912 factor H, is depicted in Formula II.

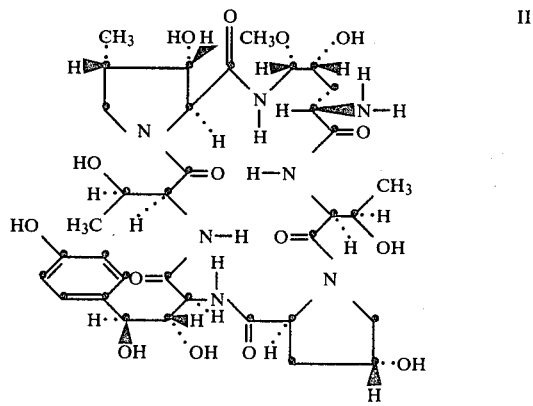

Removal of the side chain group affords a free primary α-amino group in the methoxyhydroxyornithine residue of the cyclic peptide. For convenience, the compound having the structure given in Formula II will be referred to herein as "A-30912H nucleus." As will be apparent to those skilled in the art, A-30912H nucleus can be obtained either in the form of the free amine or of the acid addition salt. Although any suitable acid addition salt may be employed, those which are non-toxic and pharmaceutically acceptable are preferred.

The method of preparing A-30912H nucleus from antibiotic A-30912 factor H by means of fermentation using *Actinoplanes utahensis* NRRL 12052 is described in the co-pending application of Bernard J. Abbott and David S. Fukuda, entitled "A-30912H NUCLEI", Ser. No. 103,016, which was filed Dec. 13, 1979. A continuation-in-part application of this application, with the corresponding Ser. No. 181,443 is being filed herewith this even date, the full disclosure of which is incorporated herein by reference. Example 4 herein, illustrates the preparation of A-30912H nucleus by fermentation using antibiotic A-30912 factor H as the substrate and *Actinoplanes utahensis* NRRL 12052 as the microorganism.

The enzyme produced by *Actinoplanes utahensis* NRRL 12052 may be the same enzyme which has been used to deacylate penicillins (see Walter J. Kleinschmidt, Walter E. Wright, Frederick W. Kavanagh, and William M. Stark, U.S. Pat. No. 3,150,059, issued Sept. 22, 1964).

Cultures of representative species of *Antinoplanaceae* are available to the public from the Northern Regional Research Laboratory under the following accession numbers:

| | |
|---|---|
| *Actinoplanes utahensis* | NRRL 12052 |
| *Actinoplanes missouriensis* | NRRL 12053 |
| *Actinoplanes sp.* | NRRL 8122 |
| *Actinoplanes sp.* | NRRL 12065 |
| *Streptosporangium roseum* var. *hollandensis* NRRL 12064 | |

The effectiveness of any given strain of microorganism within the family Actinoplanaceae for carrying out the deacylation of this invention is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a *Candida albicans* assay. Loss of antibiotic activity is an indication that the microorganism produces the requisite enzyme for deacylation. This must be verified, however, using one of the following methods: (1) analysis by HPLC for presence of the intact nucleus; or (2) reacylation with an appropriate side chain (e.g. linoleoyl, stearoyl, or palmitoyl) to restore activity.

In antibiotic A-30912 factor H, the 5-hydroxyl group present in the dihydroxyornithine residue of the peptide nucleus is methylated, while in antibiotic A-30912 factor A, the 5-hydroxyl group is unsubstituted. It will be recognized, therefore, that factor H can be made synthetically by methylating factor A using methods that are conventional for preparing an aliphatic ether from an alcohol. It will also be recognized that Factor A can be alkylated with other lower alkyl groups to form alkyl ether homologs of the factor H molecule. The alkyl ether homologs of Factor H, which can be prepared synthetically from factor A, are depicted in Formula Ia:

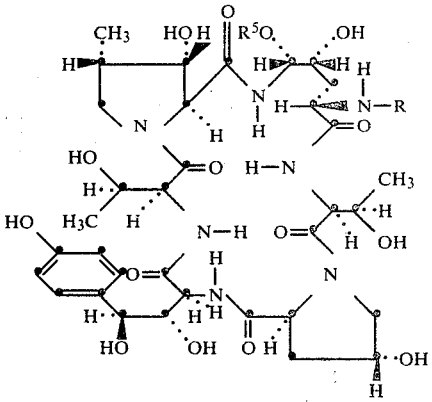

wherein $R^5$ is $C_2-C_6$ alkyl and R is linoleoyl.

It will also be apparent that the linoleoyl side chain of Factor H (Formula I) or of the homologs thereof (Formula Ia) can be hydrogenated using conventional techniques to provide tetrahydro-A-30912 factor H (Formula I, R is stearoyl) or the corresponding tetrahydro derivative of the alkyl ether homologs (Formula Ia, R is stearoyl). Alternatively, the tetrahydro derivatives (Formula I or Ia, R is stearoyl) can be made by first hydrogenating antibiotic A-30912 factor A to give tetrahydro-A-30912 factor A and then forming the desired alkyl ether derivative therefrom.

It will be understood that antibiotic A-30912 factor H, tetrahydro-A-30912 factor H, a $C_2-C_6$ alkyl ether homolog of Factor H, or a tetrahydro derivative of a $C_2-C_6$ alkyl ether homolog of Factor H can be employed as a substrate for the enzymatic deacylation using the procedures herein described.

SUMMARY OF THE INVENTION

The invention sought to be patented comprehends novel compounds derived by acylating A-30912H nucleus (Formula II) or an alkyl ether homolog thereof. The compounds of the present invention have the chemical structure depicted in Formula III:

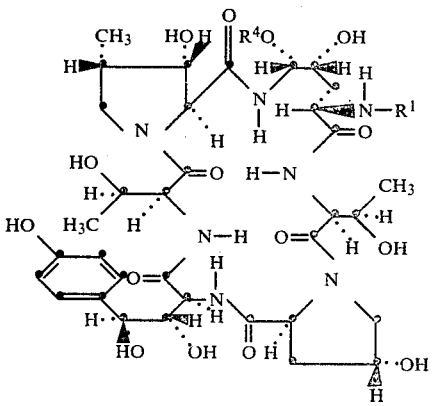

wherein $R^4$ is $C_1-C_6$ alkyl and $R^1$ is an N-alkanoyl amino acyl group of the formula

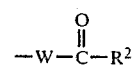

wherein:

W is a divalent aminoacyl radical of the formula:

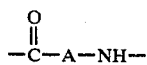  (a)

wherein A is $C_1$-$C_{10}$ alkylene or $C_5$-$C_6$ cycloalkylene;

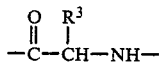  (b)

wherein $R^3$ is hydroxymethyl, hydroxyethyl, mercaptomethyl, mercaptoethyl, methylthioethyl, 2-thienyl, 3-indolemethyl, benzyl, or substituted phenyl or substituted benzyl in which the benzene ring thereof is substituted with chloro, bromo, iodo, nitro, $C_1$-$C_3$ alkyl, hydroxy, $C_1$-$C_3$ alkylthio, carbamyl, or $C_1$-$C_3$ alkylcarbamyl;

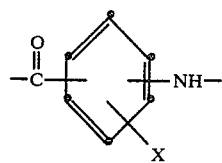  (c)

wherein X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamyl, or $C_1$-$C_3$ alkylcarbamyl;

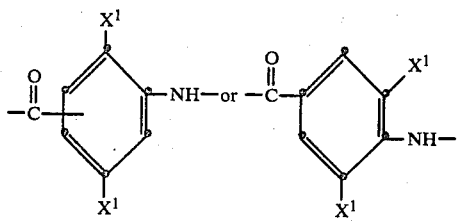  (d)

wherein $X^1$ is chloro, bromo, or iodo;

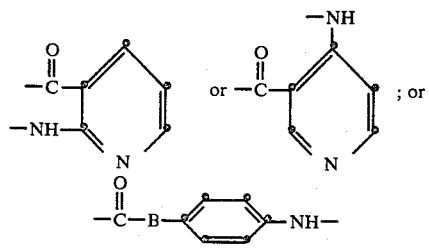  (e)

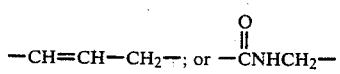  (f)

wherein B is a divalent radical of the formula: —$(CH_2)_n$—, wherein n is an integer from 1 to 3; —CH=CH—;

—CH=CH—$CH_2$—; or —$\overset{O}{\overset{\|}{C}}NHCH_2$— and $R^2$ is $C_1$-$C_{17}$ alkyl or $C_2$-$C_{17}$ alkenyl.

As employed herein the terms "alkylene", "alkyl", "alkoxy", "alkylthio", and "alkenyl" comprehend both straight and branched hydrocarbon chains. "Alkyl" means a univalent saturated hydrocarbon radical. "Alkenyl" means a univalent unsaturated hydrocarbon radical containing one, two, or three double bonds, which may be oriented in the cis or trans configuration "Alkylene" means a divalent saturated hydrocarbon radical. "Cycloalkylene" means a divalent cyclic saturated hydrocarbon radical.

Illustrative $C_1$-$C_{10}$ alkylene radicals, which are preferred for purposes of this invention are: —$CH_2$—;

in which $R^5$ is $C_1$-$C_4$ alkyl (i.e., methyl, ethyl, n-propyl, i-propyl, n-butyl, t-butyl, i-butyl, or 1-methylpropyl); —$(CH_2)$—$_m$ in which m is an integer from 2 to 10; and

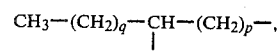

in which p is an integer from 1 to 8 and q is an integer from 0 to 7, provided that n+m must be no greater than 8.

Illustrative $C_1$-$C_{17}$ alkyl groups which are preferred for the purposes of this invention are:
(a) $CH_3$—;
(b) —$(CH_2)_nCH_3$ wherein n is an integer from 1 to 16; and
(c)

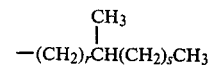

wherein r and s are independently, an integer from 0 to 14 provided that r+s can be no greater than 14.

Illustrative $C_2$-$C_{17}$ alkenyl radicals, which are preferred for the purpose of this invention, are
(a) —$(CH_2)_t$—CH=CH—$(CH_2)_u$—$CH_3$ wherein t and u are independently, an integer from 0 to 14 provided that t+u can be no greater than 14.
(b) —$(CH_2)_v$—CH=CH—$(CH_2)_y$—CH=CH—$(CH_2)_z$—$CH_3$ wherein v and z are independently, an integer from 0 to 11 and y is an integer from 1 to 12 provided that v+y+z can be no greater than 11.

In particular, the following embodiments of the $C_1$-$C_{17}$ alkyl groups are preferred:
$CH_3$—
$CH_3(CH_2)_5$—
$CH_3(CH_2)_6$—
$CH_3(CH_2)_8$—
$CH_3(CH_2)_{10}$—
$CH_3(CH_2)_{12}$—
$CH_3(CH_2)_{14}$—
$CH_3(CH_2)_{16}$—

In particular, the following embodiments of the $C_2$-$C_{17}$ alkenyl groups are preferred:
cis-$CH_3(CH_2)_5CH$=$CH(CH_2)_7$—
trans-$CH_3(CH_2)_5CH$=$CH(CH_2)_7$—
cis-$CH_3(CH_2)_{10}CH$=$CH(CH_2)_4$—
trans-$CH_3(CH_2)_{10}CH$=$CH(CH_2)_4$—
cis-$CH_3(CH_2)_7CH$=$CH(CH_2)_7$—
trans-$CH_3(CH_2)_7CH$=$CH(CH_2)_7$—
cis-$CH_3(CH_2)_5CH$=$CH(CH_2)_9$—
trans-$CH_3(CH_2)_5CH$=$CH(CH_2)_9$—
cis, cis-$CH_3(CH_2)_4CH$=$CHCH_2CH$=$CH(CH_2)_7$— trans, trans-CH$_3$(CH$_2$)$_4$CH=CHCH$_2$CH=CH(CH$_2$)$_7$—
cis,cis,cis-CH$_3$CH$_2$CH=CHCH$_2$CH=CHCH$_2$CH=CH—(CH$_2$)$_7$—.

When "W" is a divalent radical of the formula

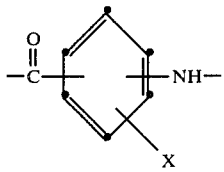

it will be recognized by those skilled in the art that the

function and the —NH— function may be oriented on the benzene ring in the ortho, meta, or para configuration relative to each other. The substituent represented by X may be substituted at any available position of the benzene ring. Preferred embodiments are those in which X is hydrogen and the

and —NH— functions are oriented in the para configuration.

The terms "substituted phenyl" and "substituted benzyl", as defined by R$_3$ in Formula III, contemplate substitution of a group at any of the available positions in the benzene ring—i.e. the substituent may be in the ortho, meta, or para configuration. The term "C$_1$–C$_3$ alkyl" as defined by R$_3$ or X in Formula III includes the methyl, ethyl, n-propyl, or i-propyl groups. Illustrative C$_1$–C$_6$ alkyl groups are methyl, ethyl, n-propyl, i-propyl, n-butyl, i-butyl, t-butyl, n-pentyl, n-hexyl, etc.

DETAILED DESCRIPTION OF THE INVENTION

The compounds of Formula III inhibit the growth of pathogenic fungi, and are useful, therefore, for controlling the growth of fungi on environmental surfaces (as an antiseptic) or in treating infections caused by fungi. In particular, the compounds are active against *Candida albicans* and are, thus especially useful for treating candidosis. The activity of the compounds can be assessed in standard microbiological test procedures, such as in vitro in agar plate disc diffusion tests or in agar tube dilution tests, or in vivo in tests in mice infected in *C. albicans*. The compounds are also active against *Trichophyton mentagrophytes* (a dermatophytic organism), *Saccharomyces pastorianus,* and *Neurospora crassa.*

The compounds of Formula III are prepared by acylating A-30912H nucleus or an alkyl ether homolog thereof at the α-amino group of dihydroxyornithine with the appropriate N-alkanoyl aminoacyl or N-alkenoyl amino acyl side chain using methods conventional in the art for forming an amide bond. The acylation is accomplished, in general, by reacting the nucleus with an activated derivative of the acid (Formula IV) corresponding to the desired acyl side chain group.

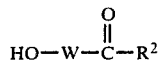

(W and R$^2$ have the meaning described herein supra). By the term "activated derivative" is meant a derivative which renders the carboxyl function of the acylating agent reactive to coupling with the primary amino group to form the amide bond which links the acyl side chain to the nucleus. Suitable activated derivatives, their methods of preparation, and their methods of use as acylating agents for a primary amine will be recognized by those skilled in the art. Preferred activated derivatives are: (a) an acid halide (e.g. acid chloride), (b) an acid anhydride (e.g. an alkoxyformic acid anhydride or aryloxyformic acid anhydride) or (c) an activated ester (e.g. a 2,4,5-trichlorophenyl ester, a N-hydroxybenztriazole ester, or an N-hydroxysuccinimide ester). Other methods for activating the carboxyl function include reaction of the carboxylic acid with a carbonyldiimide (e.g. N,N-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of Formula III is by the active ester method. The use of the 2,4,5-trichlorophenyl ester of the desired N-alkanoylamino acid or N-alkenoylamino acid (Formula IV) as the acylating agent is most preferred. In this method, an excess amount of the active ester is reacted with the nucleus at room temperature in a nonreactive organic solvent such as dimethyl formamide (DMF). The reaction time is not critical, although a time of about 15 to about 18 hours is preferred. At the conclusion of the reaction, the solvent is removed, and the residue is purified such as by column chromatography using silica gel as the stationary phase and a mixture of ethyl acetate/methanol (3:2, v/v) as the solvent system.

The 2,4,5-trichlorophenyl esters of the N-alkanoylamino acids or N-alkanoylamino acids can be prepared conveniently by treating the desired amino acid (Formula IV) with 2,4,5-trichlorophenol in the presence of a coupling agent, such as N,N'dicyclohexylcarbodiimide. Other methods suitable for preparing amino acid esters will be apparent to those skilled in the art.

Another method for preparing the compounds of Formula III is by: (a) deacylating antibiotic A-30912 factor A enzymatically using *Actinoplanes utahenisis* NRRL 12052 as described in the co-pending application of Bernard J. Abbott and David S. Fukuda, entitled "A-30912A Nucleus", Ser. No. 103,017, which was filed Dec. 13, 1979. A continuation-in-part application of this application, with the corresponding Ser. No. 181,029, is being filed herewith this even date, the full disclosure of which is incorporated herein by reference (b) acylating A-30912A nucleus so produced with the appropriate side chain acyl group using the methods hereinbefore described with respect to the acylation of A-30912H nucleus, and (c) alkylating the appropriate acyl derivative of the A-30912A nucleus to form the desired alkyl ether derivative. The alkylation (Step C) can be performed using methods that are conventional for making an aliphatic ether from an alcohol. For example, the appropriate acyl derivative of A-30912A nucleus can be methylated by treating a solution of the derivative in an inert organic solvent (e.g. dimethylformamide) with methanol in the presence of an organic acid (e.g. 3% HCl-methanol). The product can be isolated by conventional methods and purified by reversed-phase HPLC.

The N-alkanoylamino acids or N-alkenoylamino acids are either known compounds or they can be made by acylating the appropriate amino acid with the appropriate alkanoyl or alkenoyl group using conventional methods, such as those described herein supra. A preferred way of preparing the N-alkanoylamino acids is by treating the appropriate amino acid with an alkanoic acid chloride in pyridine. The alkanoic acids, the activated derivatives thereof, and the amino acids employed in the preparation of the products of this invention are either known compounds or they can be made by known methods or by modification of known methods which will be apparent to those skilled in the art.

If a particular amino acid contains an acylable functional group other than the amino group, it will be understood by those skilled in the art that such a group must be protected prior to reaction of the amino acid with the reagent employed to attach the alkanoyl or alkenoyl group. Suitable protecting groups can be any group known in the art to be useful for the protection of a side chain functional group in peptide synthesis. Such groups are well known, and the selection of a particular protecting group and its method of use will be readily known to one skilled in the art [see, for example, "Protective Groups In Organic Chemistry", M. McOmie, Editor, Plenum Press, N.Y., 1973].

It will be recognized that certain amino acids employed in the synthesis of the products of this invention may exist in optically active forms, and both the natural configuration (L-configuration) and unnatural configuration (D-configuration) may be employed as starting materials and will give products which are within the contemplation of this invention.

When employed systemically, the dosage of the compounds of Formula III will vary according to the particular compound being employed, the severity and nature of the infection, and the physical condition of the subject being treated. Therapy should be initiated at low dosages, the dosage being increased until the desired antifungal effect is obtained. The compounds can be administered intravenously or intramuscularly by injection in the form of a sterile aqueous solution or suspension to which may be added, if desired, various conventional pharmaceutically acceptable preserving, buffering, solubilizing, or suspending agents. Other additives, such as saline or glucose may be added to make the solutions isotonic. The proportions and nature of such additives will be apparent to those skilled in the art.

When employed to treat vaginal candida infections, the compounds of Formula III can be administered in combination with pharmaceutically acceptable conventional excipients suitable for intravaginal use. Formulations adapted for intravaginal administration will be known to those skilled in the art.

One of the methods of making and using the compounds of the present invention is illustrated in the following examples:

EXAMPLE 1

The following procedure, which give the preparation of the compound of Formula III wherein $R^1$ is N-(n-dodecanoyl)-p-aminobenzoyl, illustrates a method of preparation of the compounds of Formula III.

A. Preparation of N-(n-dodecanoyl)-p-aminobenzoic acid n-Dodecanoyl chloride (8.74 g.; 40 mmoles) is added dropwise to a solution of p-aminobenzoic acid (40 mmoles) dissolved in pyridine (100 ml.). The mixture is stirred for 3 hours and poured into water (3 l.). The precipitate which forms is filtered and dried in vacuo to give N-(n-dodecanoyl)-p-aminobenzoic acid (11.01 g.).

B. Preparation of the 2,4,5-trichlorophenyl ester of N-(dodecanoyl)-p-aminobenzoic acid N-(n-Dodecanoyl)-p-aminobenzoic acid (11.01 g.; 34.5 mmoles), 2,4,5-trichlorophenol (7.5 g.; 38 mmoles), and dicyclohexylcarbodiimide (6.94 g.; 34.5 mmoles) are dissolved in methylene chloride (250 ml). The mixture is stirred at room temperature for 3.5 hours and then filtered. The filtrate is evaporated in vacuo to give a residue which is crystallized from acetonitrile/water to afford the 2,4,5-trichlorophenyl ester of N-(n-dodecanoyl)-p-aminobenzoic acid (12.84 g.).

C. Acylation of A-30912H nucleus

A-30912H nucleus (10.2 mmoles) and the 2,4,5-trichlorophenyl ester of N-(n-dodecanoyl)-p-aminobenzoic acid (10.2 mmoles) are dissolved in dimethylformamide (100 ml.). The solution is stirred at room temperature for 15 hours. Solvent is removed in vacuo to give a residue which is washed twice with diethylether. The washes are discarded. The washed residue is dissoled in methanol (50 ml.) and is purified by reversed phase HPLC by means of a "Prep LC/System 500" unit (Waters Associates, Inc., Milford, Mass.) using a Prep Pak-500/C18 column (Water Associates, Inc.) as the stationary phase. The column is eluted isocratically with $H_2O/CH_3OH/CH_3CN$ (25:65:10 v/v) at 500 psi. The fractions are analyzed by TLC using silica gel plates and $H_2O/CH_3OH/CH_3CN$ (25:65:10 v/v) as the solvent system. Fractions containing the desired product are combined and lyophilized to give the N-(n-dodecanoyl)-p-aminobenzoyl derivative of A-30912H nucleus.

EXAMPLE 2

The method described in Example 1, with minor changes, can be used to synthesize additional derivatives of the A30912H nucleus. The substitution of the appropriate acyl chloride and amino acid in Step A, the substitution of the appropriate N-alkanoyl amino acid, (plus the use of tetrahydrofuran as the solvent for N-alkanoyl monochloro-substituted aminobenzoic acids), in Step B, and the substitution of the appropriate 2,4,5-trichlorophenyl ester in Step C of Example 1 can yield the derivatives of the A30912H nucleus shown below:

N-Alkanoylamino Acid Derivatives of A-30912H Nucleus
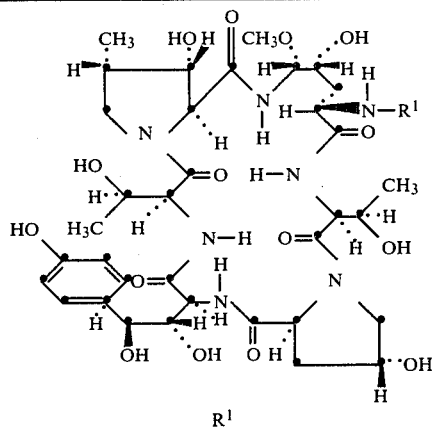
R¹
CH₃(CH₂)₁₀CONHCH(CH₂C₆H₅)CO—
CH₃(CH₂)₁₀CONH(CH₂)₄—CO—
(CH₃(CH₂)₁₀CONH(CH₂)₁₀—CO—
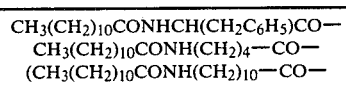
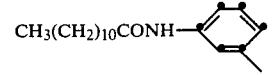
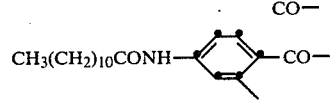
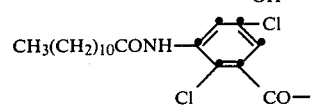
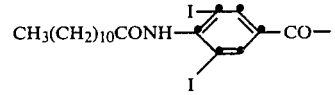
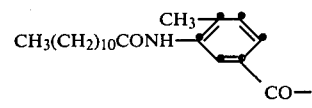
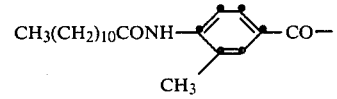
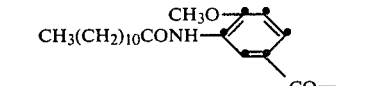
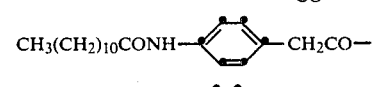
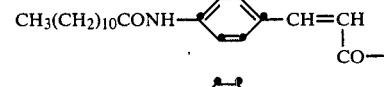
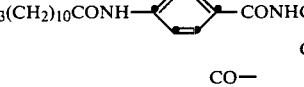
CH₃(CH₂)₅CONH(CH₂)₁₀—CO—
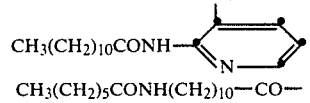
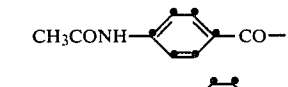
-continued
N-Alkanoylamino Acid Derivatives of A-30912H Nucleus
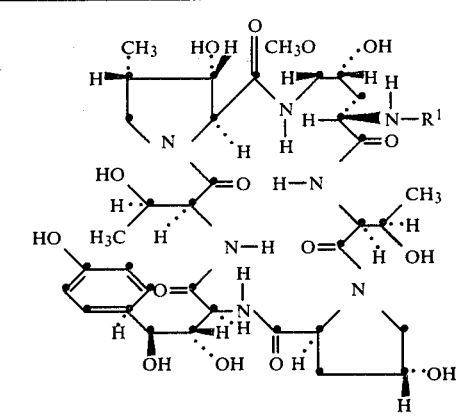
R¹
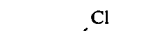
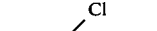
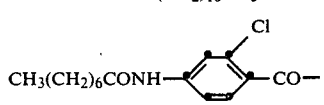
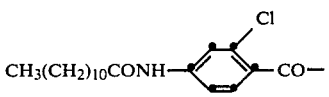

N-Alkanoylamino Acid Derivatives of A-30912H Nucleus

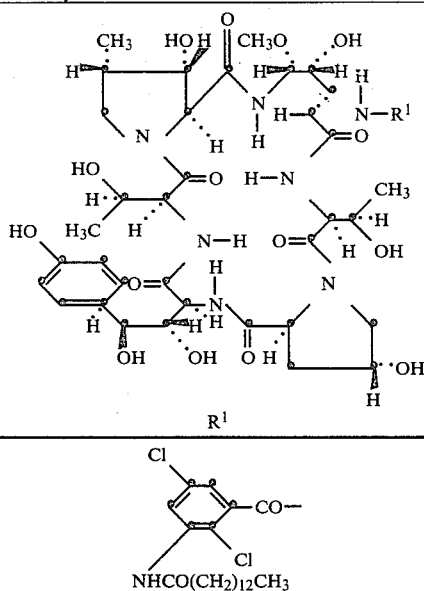

| | |
|---|---|
| R¹ | |

Cl—C₆H₂(Cl)—CO—  
NHCO(CH₂)₁₂CH₃

EXAMPLE 3

The following procedure illustrates the preparation of the N-(n-dodecanoyl)-p-aminobenzoyl derivative of A-30912H nucleus form A-30912A nucleus.

A-30912A nucleus is treated with 2,4,5-trichlorophenyl N-(n-dodecanoyl)-p-aminobenzoate according to the procedure of Example 1. The derivative thus obtained is methylated by treating a sample (20 mg) with 3% HCl-methanol (0.06 ml) in dimethylformamide. The solution is allowed to stand with stirring for 16 hours afterwhich the solvent is removed under reduced pressure and a residue is obtained. The residue is purified by reversed-phase HPLC using silica gel/C₁₈ resin.

EXAMPLE 4

Preparation of A-30912H Nucleus

A. Fermentation of Actinoplanes utahensis

A stock culture of *Actinoplanes utahensis* NRRL 12052 is prepared and maintained on an agar slant. The medium used to prepare the slant is selected from one of the following:

| MEDIUM A | |
|---|---|
| Ingredient | Amount |
| Baby oatmeal | 60.0 g |
| Yeast | 2.5 g |
| K₂HPO₄ | 1.0 g |
| Czapek's mineral stock* | 5.0 ml |
| Agar | 25.0 g |
| Deionized water | q.s. to 1 liter | pH before autoclaving is about 5.9; adjust to pH 7.2 by addition of NaOH; after autoclaving, pH is about 6.7.
*Czapek's mineral stock has the following composition:

| Ingredient | Amount |
|---|---|
| FeSO₄ . 7H₂O (dissolved in 2 ml conc HCl) | 2 g |
| KCl | 100 g |
| MgSO₄ . 7H₂O | 100 g |
| Deionized water | q.s. to 1 liter |

MEDIUM B

-continued

| Ingredient | Amount |
|---|---|
| Potato dextrin | 5.0 g |
| Yeast extract | 0.5 g |
| Enzymatic hydrolysate of casein* | 3.0 g |
| Beef extract | 0.5 g |
| Dextrose | 12.5 g |
| Corn starch | 5.0 g |
| Meat peptone | 5.0 g |
| Blackstrap molasses | 2.5 g |
| MgSO₄ . 7H₂O | 0.25 g |
| CaCO₃ | 1.0 g |
| Czapek's mineral stock | 2.0 ml |
| Agar | 20.0 g |
| Deionized water | q.s. to 1 liter |

*N—Z—Amine A, Humko Sheffield Chemical, Lyndhurst, N.J.

The slant is inoculated with *Actinoplanes utahensis* NRRL 12052, and is the inoculated slant is incubated at 30° C. for about 8 to 10 days. About ½ of the slant growth is used to inoculate 50 ml of a vegetative medium having the following composition:

| Ingredient | Amount |
|---|---|
| Baby oatmeal | 20.0 g |
| Sucrose | 20.0 g |
| Yeast | 2.5 g |
| Distiller's Dried Grain* | 5.0 g |
| K₂HPO₄ | 1.0 g |
| Czapek's mineral stock | 5.0 ml |
| Deionized water | q.s. to 1 liter | adjust to pH 7.4 with NaOH; after autoclaving, pH is about 6.8.
*National Distillers Products Co., 99 Park Ave., New York, N.Y.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen", *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (800 ml), prepared as above-described, is used to inoculate 100 liters of sterile production medium selected from one of the following:

| MEDIUM I | |
|---|---|
| Ingredient | Amount (g/L) |
| Peanut meal | 10.0 |
| Soluble meat peptone | 5.0 |
| Sucrose | 20.0 |
| $KH_2PO_4$ | 0.5 |
| $K_2HPO_4$ | 1.2 |
| $MgSO_4 \cdot 7H_2O$ | 0.25 |
| Tap water | q.s. to 1 liter |

The pH of the medium is about 6.9 after sterilization by autoclaving at 121° C. for 45 minutes at about 16–18 psi.

| MEDIUM II | |
|---|---|
| Ingredient | Amount (g/L) |
| Sucrose | 30.0 |
| Peptone | 5.0 |
| $K_2HPO_4$ | 1.0 |
| KCl | 0.5 |
| $MgSO_4 \cdot 7H_2O$ | 0.5 |
| $FeSO_4 \cdot 7H_2O$ | 0.002 |
| Deionized water | q.s. to 1 liter |

Adjust to pH 7.0 with HCl; after autoclaving, pH is about 7.0.

| MEDIUM III | |
|---|---|
| Ingredient | Amount (g/L) |
| Glucose | 20.0 |
| $NH_4Cl$ | 3.0 |
| $Na_2SO_4$ | 2.0 |
| $ZnCl_2$ | 0.019 |
| $MgCl_2 \cdot 6H_2O$ | 0.304 |
| $FeCl_3 \cdot 6H_2O$ | 0.062 |
| $MnCl_2 \cdot 4H_2O$ | 0.035 |
| $CuCl_2 \cdot 2H_2O$ | 0.005 |
| $CaCO_3$ | 6.0 |
| $KH_2PO_4$* | 0.67 |
| Tap water | q.s. to 1 liter |

*Sterilized separately and added aseptically Final pH about 6.6.

The inoculated production medium is allowed to ferment in a 165-liter fermentation tank at a temperature of about 30° C. for about 42 hours. The fermentation medium is stirred with conventional agitators at about 200 RPM and aerated with sterile air to maintain the dissolved oxygen level abobe 30% of air saturation at atmospheric pressure.

B. Deacylation of Antibiotic A-30912 Factor H

A fermentation of *A. utahensis* is carried out as described in Sect. A, using production medium I. After the culture is incubated for about 48 hours, A-30912 factor H, dissolved in a small amount of methanol, is added to the fermentation medium.

Deacylation of A-30912 factor H is monitored by paper-disc assay against *Candida albicans* or *Neurospora crassa*. The fermentation is allowed to continue until deacylation is complete as indicated by disappearance of activity.

C. Isolation of A-30912H Nucleus

Whole fermentation broth, obtained as described in Sect. B, is filtered. The mycelial cake is discarded. The clear filtrate thus obtained is passed through a column containing HP-20 resin (DIAION High Porous Polymer, HP-Series, Mitsubishi Chemical Industries Limited, Tokyo, Japan). The effluent thus obtained is discarded. The column is then washed with up to eight column volumes of deionized water at pH 6.5–7.5 to remove residual filtered broth. This wash water is discarded. The column is then eluted with a water:methanol (7:3) solution. Elution is monitored using the following procedure: Two aliquots are taken from each eluted fraction. One of the aliquots is concentrated to a small volume and is treated with an acid chloride such as myristoyl chloride. This product and the other (untreated) aliquot are assayed for activity against *Candida albicans*. If the untreated aliquot does not have activity and the acylated aliquot does have activity, the fraction contains A-30912H nucleus. The eluate containing A-30912H nucleus is concentrated under vacuum to a small volume and lyophilized to give crude nucleus.

D. Purification of A-30912H Nucleus by Reversed-Phase Liquid Chromatography

Crude A-30912H nucleus, obtained as described in Section C, is dissolved in water:acetonitrile:acetic acid:-pyridine (96:2:1:1). This solution is chromatographed on a column filled with Lichroprep RP-18, particle size 25–40 microns (MC/B Manufacturing Chemists, Inc. E/M, Cincinnati, OH). The column is part of a Chromatospac Prep 100 unit (Jobin Yvon, 16–18 Rue du Canal 91160 Longjumeau, France). The column is operated at a pressure of 90–100 psi, giving a flow rate of about 60 ml/minute, using the same solvent. Separation is monitored at 280 nm using a UV monitor (ISCO Absorption Monitor Model UA-5, Instrumentation Specialties Co., 4700 Superior Ave., Lincoln, Neb. 68504) with an optical unit (ISCO Type 6).

EXAMPLE 5

A-30912H nucleus is prepared and purified by the method of Example 4 except that tetrahydro-A-30912H is used as the substrate.

EXAMPLE 6

Preparation of the A-42355 Antibiotic Complex

A. Shake-Flask Fermentation

A culture of *Aspergillus nidulans* var. *roseus* NRRL 11440 is prepared and maintained on an agar slant prepared with medium having the following composition:

| Ingredient | Amount |
|---|---|
| Glucose | 5 g |
| Yeast extract | 2 g |
| $CaCO_3$ | 3 g |
| Vegetable juice* | 200 ml |
| Agar** | 20 g |
| Deionized water | q.s. to 1 liter |

(initial pH 6.1)
*V-8 Juice, Campbell Soup Co., Camden, N.J.
**Meer Corp.

The slant is inoculated with *Aspergillus nidulans* var. *roseus* NRRL 11440, and the inoculated slant is incubated at 25° C. for about seven days. The mature slant culture is covered with water and scraped with a sterile loop to loosen the spores. The resulting suspension is further suspended in 10 ml of sterile deionized water.

One ml of the suspended slant growth is used to inoculate 55 ml of vegetative medium in a 250-ml flask. The vegetative medium has the following composition:

| Ingredient | Amount |
|---|---|
| Sucrose | 25 g |
| Blackstrap molasses | 36 g |
| Corn-steep liquor | 6 g |

| Ingredient | Amount |
| --- | --- |
| Malt extract | 10 g |
| K₂HPO₄ | 2 g |
| Enzymatic hydrolysate of casein* | 10 g |
| Tap water | 1100 ml |

(initial pH 6.5-6.7)
*N-Z-Case, Humko Sheffield Chemical, Lyndhurst, N.J.

The inoculated vegetative medium is incubated at 25° C. for 48 hours at 250 rpm on a rotary-type shaker. After 24 hours, the medium is homogenized for one minute at low speed in a blender (Waring type) and then returned to incubation for the remaining 24 hours. Alternatively, the inoculated vegetative medium can be incubated for 48 hours and then homogenized for 15 seconds at low speed.

This incubated vegetative medium may be used to inoculate shake-flask fermentation culture medium or to inoculate a second-stage vegetative medium. Alternatively, it can be stored for later use by maintaining the culture in the vapor phase of liquid nitrogen. The culture is prepared for such storage in multiple small vials as follows: The vegetative cultures are mixed volume/volume with a suspending solution having the following composition:

| Ingredient | Amount |
| --- | --- |
| Glycerol | 20 ml |
| Lactose | 10 g |
| Deionized water | q.s. to 100 ml |

The prepared suspensions are distributed in small sterile screw-cap tubes (4 ml per tube). These tubes are stored in the vapor phase of liquid nitrogen.

A stored suspension thus prepared can be used to inoculate either agar slants or liquid seed media. Slants are incubated at 25° C. in the light for 7 days.

B. Tank Fermentation

In order to provide a larger volume of inoculum, 10 ml of incubated first-stage vegetative culture is used to inoculate 400 ml of a second-stage vegetative growth medium having the same composition as that of the vegetative medium. The second-stage medium is incubated in a two-liter wide-mouth Erlenmeyer flask at 25° C. for 24 hours on a shaker rotating through an arc two inches in diameter at 250 rpm.

Incubated second-stage medium (800 ml), prepared as above described, is used to inoculate 100 liters of sterile production medium selected from one of the following:

| MEDIUM IV | |
| --- | --- |
| Ingredient | Amount |
| ZnSO₄ . 7H₂O | 0.00455 g/L |
| Soluble meat peptone* | 30.5 g/L |
| Soybean meal | 15.5 g/L |
| Tapioca dextrin** | 2.0 g/L |
| Blackstrap molasses | 10.5 g/L |
| Enzymatic hydrolysate of casein*** | 8.5 g/L |
| Na₂HPO₄ | 4.5 g/L |
| MgSO₄ . 7H₂O | 5.5 g/L |
| FeSO₄ . 7H₂O | 0.1 g/L |
| Cottonseed oil | 40.0 ml |
| (Antifoam)**** | 1.0 ml |
| Tap water | 1000.0 ml |

(initial pH 6.8-7.0)
*O.M. Peptone, Amber Laboratories, Juneau Wisc.
**Stadex 11, A.E. Staley Co., Decatur, Ill.
***N-Z-Amine A, Humko Sheffield Chemical, Lyndhurst, N.J.
****P2000, Dow Corning, Midland, Michigan

| MEDIUM V | |
| --- | --- |
| Ingredient | Amount |
| Glucose | 2.5% |
| Starch | 1.0% |
| Soluble meat peptone* | 1.0% |
| Blackstrap molasses | 1.0% |
| CaCO₃ | 0.2% |
| MgSO₄ . 7H₂O | 0.05% |
| Enzymatic hydrolysate of casein** | 0.4% |
| (Antifoam)*** | 0.02% |
| Tap water | q.s. to volume |

*O.M. Peptone
**N-Z-Amine A
***Antifoam "A", Dow Corning

The inoculated production medium is allowed to ferment in a 165-liter fermentation tank at a temperature of 25° C. for about 7 days. The fermentation medium is aerated with sterile air, maintaining the dissolved oxygen level about approximately 50 percent of air saturation.

C. Third-Stage Vegetative Medium

Whenever the fermentation is carried out in tanks larger than those used for 100-liter fermentation, it is recommended that a third-stage vegetative culture be used to seed the larger tank. A preferred third-stage vegetative medium has the following composition:

| Ingredient | Amount |
| --- | --- |
| Sucrose | 25 g |
| Blackstrap molasses | 25 g |
| Corn-steep liquor | 6 g |
| Enzymatic hydrolysate of casein* | 10 g |
| Malt extract | 10 g |
| K₂HPO₄ | 2 g |
| Tap water | 1000 ml |

(initial pH 6.1)
*N-Z-Case

EXAMPLE 7

Separation of the A-42355 Antibiotic Complex

Whole fermentation broth (4127 liters), obtained by the method described in Example 6 using production medium V, is stirred thoroughly with methanol (4280 liters) for one hour and then is filtered, using a filter aid (Hyflo Super-cel, a diatomaceous earth, Johns-Manville Products Corp.). The pH of the filtrate is adjusted to pH 4.0 by the addition of 5 N HCl. The acidified filtrate is extracted twice with equal volumes of chloroform. The chloroform extracts are combined and concentrated under vacuum to a volume of about 20 liters. This concentrate is added to about 200 liters of diethyl ether to precipitate the A-42355 complex. The precipitate is separated by filtration to give 2775 g of the A-42355 complex as a gray-white powder.

EXAMPLE 8

Isolation of A-30912 Factor H

A-42355 antibiotic complex (5.0 g), prepared as described in Example 7, is dissolved in 35 ml of methanol:water:acetonitrile (7:2:1); the resulting solution is filtered and introduced onto a 3.7-cm I.D.×42-cm glass column (Michel-Miller Column) through a loop with the aid of a valve system. The column is packed with LP-1/$C_{18}$ silica gel reversed phase resin (10-20 microns) in methanol:water:acetonitrile (7:2:1) (Example 9) as described in Example 10. The solvent is moved through the column at a flow rate of 13 ml/min at ca. 120 psi, using an F.M.I. pump with valveless piston design and collecting one fraction every two minutes. Elution of the antibiotic is monitored by UV at 280 nm as described in Example 4, Sect. D. Fractions 112-132 are combined with fractions 106-117 from a second similar purification. The combined fractions are concentrated under vacuum to an oil. The oil is dissolved in a small volume of tert-butanol and lyophilized to give 173 mg of crude A-30912 factor H.

The crude A-30912 factor H (150 mg) is dissolved in 8 ml of methanol:water:acetonitrile (7:2:1); the resulting solution is filtered and introduced onto a 2.0-cm I.D.×32-cm glass column, as described above. The solvent is moved through the column at a flow rate of 8 ml/min at ca. 80 psi collecting one fraction every three minutes. Elution of the antibiotic is monitored at 280 nm. Fractions 17 and 18 are combined and concentrated under vacuum to give an oil. The oil is dissolved in a small volume of tert-butanol and lyophilized to give 29 mg of A-30912 factor H.

The individual A-30912 factors can be identified by the use of thin-layer chromatography (TLC). The $R_f$ values of A-30912 factors A-G, using silica gel (Merck, Darmstadt) TLC, a benzene:methanol (7:3) solvent system, and *Candida albicans* bioautography are given in Table I.

TABLE I

| A-30912 Factor | $R_f$ Value |
|---|---|
| A | 0.35 |
| B | 0.45 |
| C | 0.54 |
| D | 0.59 |
| E | 0.27 |
| F | 0.18 |
| G | 0.13 |

The approximate $R_f$ values of A-30912 factors A, B, C, D, and H in different solvent systems, using silica gel TLC (Merck-Darmstadt silica gel #60 plates, 20×20 cm) and *Candida albicans* bioautography, are given in Table II.

TABLE II

| A-30912 Factor | $R_f$ Values - Solvent Systems | | | |
|---|---|---|---|---|
|  | a | b | c | d |
| Factor A | 0.28 | 0.14 | 0.28 | 0.43 |
| Factor B | 0.39 | 0.21 | 0.42 | 0.47 |
| Factor C | 0.46 | 0.31 | 0.51 | 0.58 |
| Factor D | 0.50 | 0.38 | 0.57 | 0.61 |
| Factor H | 0.42 | 0.27 | 0.36 | 0.53 |

Solvent Systems
a ethyl acetate:methanol (3:2)
b ethyl acetate:methanol (7:3)
c acetonitrile:water (95:5)
d ethyl acetate:ethanol:acetic acid (40:60:0.25)

A-30912 factors A, B, D and H can also be identified by analytical HPLPLC using the following conditions:

| | |
|---|---|
| Column: | glass, 0.8 × 15.0 cm |
| Packing: | Nucleosil ® 10—$C_{18}$ (Machery-Nagel and Company); packed using slurry-packing procedure of Example 8 |
| Solvent: | methanol:water:acetonitrile (7:2:1) |
| Sample Volume: | 8 mcl |
| Sample Size: | 8 mcg |
| Column Temperature: | ambient |
| Flow Rate: | 1.8 ml/min |
| Pressure: | ca. 200 psi |
| Detector: | UV at 222 nm (ISCO Model 1800 Variable Wavelength UV-Visible Absorbance Monitor) |
| Pump: | LDC Duplex Minipump |
| Injection: | loop injection |

The approximate retention times for A-30912 factors A, B, D, and H under these conditions are summarized in Table III.

TABLE III

| A-30912 Factor | Retention Time (seconds) |
|---|---|
| A | 792 |
| B | 870 |
| H | 990 |
| D | 1,140 |

EXAMPLE 9

Preparation of Silica Gel/$C_{18}$ Reversed Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) in a 5-L round-bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azeotrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 L) and acetone (3 L), and then air-dried overnight (16-20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring carefully. The final product is recovered by filtration, washed with toluene (3 L) and methanol (6 L), and then dried under vacuum at 50° C. overnight (16-20 hours).

EXAMPLE 10

Slurry Packing Procedure for Michel-Miller Columns

General Information

This procedure is employed for packing silica gel $C_{18}$ reversed phase resin such as that prepared by the method of Example 9.

Generally, a pressure of less than 200 psi and flows rates between 5-40 ml/minute are required for this slurry packing technique; this is dependent on column volume and size. Packing pressure should exceed the pressure used during actual separation by 30-50 psi; this will assure no further compression of the adsorbent during separation runs.

A sudden decrease in pressure may cause cracks or channels to form in the packing material, which would greatly reduce column efficiency. Therefore, it is important to let the pressure drop slowly to zero whenever the pump is turned off.

The approximate volume of columns (Ace Glass Cat. No., unpacked) are No. 5795-04, 12 ml; No. 5795-10, 110 ml; No. 5795-16, 300 ml; No. 5759-24, 635 ml; and No. 5796-34, 34 ml.

The time required to pack a glass column will vary from minutes to several hours depending on column size and the experience of the scientist.

EXAMPLE

1. Connect glass column to a reservoir column via coupling (volume of reservoir column should be twice that of the column). Place both columns in vertical positions (reservoir column above).
2. Weigh out packing material (ca. 100 g for 200 ml column).
3. Add ca. five volumes of solvent to packing material; use a mixture of 70-80% methanol and 20-30% water.
4. Shake well until all particles are wetted, let stand overnight or longer to assure complete soaking of particles by solvent. Decant supernatant liquid.
5. Slurry the resin with sufficient solvent to fill reservoir column. Pour swiftly into reservoir. The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.
6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solvent-delivery system is used (ca. 20 ml/minute).
7. Continue until column is completely filled with adsorbent. Pressure should not exceed maximum tolerance of column during this operation (ca. 200 psi for large columns and 300 psi for analytical columns). In most cases, pressures less than 200 psi will be sufficient.
8. Should pressure exceed maximum values, reduce flow-rate; pressure will drop.
9. After column has been filled with adsorbent, turn off pump; let pressure drop to zero; disconnect reservoir; replace reservoir with a pre-column; fill pre-column with solvent and small amount of adsorbent; and pump at maximum pressure until column is completely packed. For additional information, see general procedure. Always allow pressure to decrease slowly after turning off pump--this will prevent formation of any cracks or channels in the packing material.
10. Relieve pressure and disconnct pre-column carefully. With small spatula remove a few mm (2-4) of packing from top of column; place 1 or 2 filter(s) in top of column; gently depress to top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

EXAMPLE 11

Preparation of Tetrahydro-A-30912H

A-30912 factor H is dissolved in ethanol. $PtO_2$ in absolute ethanol is reduced to form Pt, which in turn is used to reduce the A-30912 factor H catalytically, using hydrogenation under positive pressure until the reaction is complete (about 2-3 hours). The reaction mixture is filtered and concentrated under vacuum. The residue is dissolved in a small amount of tert-butanol and lyophilized to give tetrahydro-A-30912H.

What is claimed is:
1. A compound of the formula:

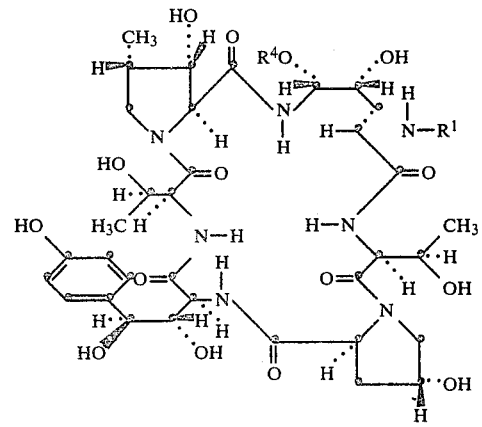

wherein $R^4$ is $C_1$-$C_6$ alkyl and $R^1$ is an N-alkanoyl amino acyl group of the formula

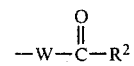

wherein:
W is a divalent aminoacyl radical of the formula:

(a) 

wherein A is $C_1$–$C_{10}$ alkylene or $C_5$–$C_6$ cycloalkylene;

(b) 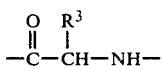

wherein $R^3$ is hydroxymethyl, hydroxyethyl, mercaptomethyl, mercaptoethyl, methylthioethyl, 2-thienyl, 3-indolemethyl, phenyl, benzyl, or substituted phenyl or substituted benzyl in which the benzene ring thereof is substituted with chloro, bromo, iodo, nitro, $C_1$–$C_3$ alkyl, hydroxy, $C_1$–$C_3$ alkylthio, carbamyl, or $C_1$–$C_3$ alkylcarbamyl;

(c) 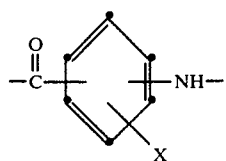

wherein X is hydrogen, chloro, bromo, iodo, nitro, $C_1$–$C_3$ alkyl, hydroxy, $C_1$–$C_3$ alkoxy, mercapto, $C_1$–$C_3$ alkylthio, carbamyl, or $C_1$–$C_3$ alkylcarbamyl;

(d) 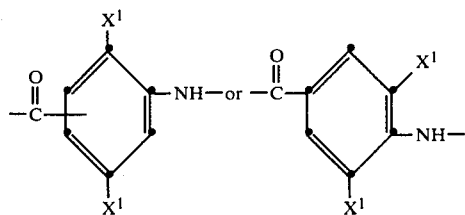

wherein $X^1$ is chloro, bromo, or iodo;

(e) 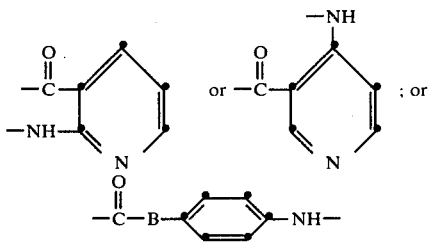

(f) 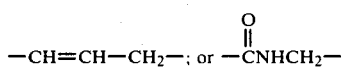

wherein B is a divalent radical of the formula: —(CH$_2$)$_n$—, wherein n is an integer from 1 to 3; —CH=CH—;

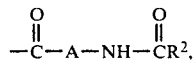

and $R^2$ is $C_1$–$C_{17}$ alkyl or $C_2$–$C_{17}$ alkenyl.

2. A compound as defined in claim 1 wherein $R^1$ is $$-\overset{O}{\underset{\|}{C}}-A-NH-\overset{O}{\underset{\|}{C}}R^2,$$

wherein A is $C_1$–$C_{10}$ alkylene and $R^2$ is straight chain $C_1$–$C_{17}$ alkyl, and $R^4$ is methyl.

3. The compound as defined in claim 2 wherein $R^1$ is N-(n-dodecanoyl)-5-amino-n-pentanoyl.

4. The compound as defined in claim 2 wherein $R^1$ is N-(n-dodecanoyl)-11-amino-n-hendecanoyl.

5. The compound as defined in claim 2 wherein $R^1$ is N-(n-heptanoyl)-11-amino-n-hendecanoyl.

6. A compound as defined in claim 1 wherein $R^1$ is

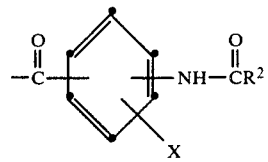

wherein X is hydrogen and $R^2$ is straight chain $C_1$–$C_{17}$ alkyl, and $R^4$ is methyl.

7. The compound as defined in claim 6 wherein $R^1$ is N-(n-dodecanoyl)-p-aminobenzoyl.

8. The compound as defined in claim 6 wherein $R^1$ is N-(n-dodecanoyl)-m-aminobenzoyl.

9. The compound as defined in claim 6 wherein $R^1$ is N-(acetyl)-p-aminobenzoyl.

10. The compound as defined in claim 6 wherein $R^1$ is N-(n-heptanoyl)-p-aminobenzoyl.

11. The compound as defined in claim 6 wherein $R^1$ is (N-(n-decanoyl)-p-aminobenzoyl.

12. The compound as defined in claim 6 wherein $R^1$ is N-(n-tetradecanoyl)-p-aminobenzoyl.

13. The compound as defined in claim 6 wherein $R^1$ is N-(n-hexadecanoyl)-p-aminobenzoyl.

14. A compound as defined in claim 1 wherein $R^1$ is

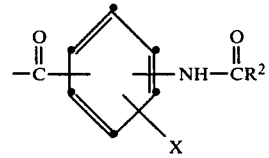

wherein X is chloro, bromo, iodo, nitro, $C_1$–$C_3$ alkyl, hydroxy, $C_1$–$C_3$ alkoxy, mercapto, $C_1$–$C_3$ alkylthio, carbamoyl, or $C_1$–$C_3$ alkylcarbamoyl and $R^2$ is straight chain $C_1$–$C_{17}$ alkyl; and $R^4$ is methyl.

15. The compound as defined in claim 14 wherein $R^1$ is N-(n-dodecanoyl)-4-amino-2-hydroxybenzoyl.

16. The compound as defined in claim 14 wherein $R^1$ is N-(n-dodecanoyl)-3-amino-4-methylbenzoyl.

17. The compound as defined in claim 14 wherein $R^1$ is N-(n-dodecanoyl)-4-amino-3-methylbenzoyl.

18. The compound as defined in claim 14 wherein $R^1$ is N-(n-dodecanoyl)-3-amino-4-methoxybenzoyl.

19. The compound as defined in claim 1 wherein $R^1$ is N-(n-dodecanoyl)-3-amino-2,5-dichlorobenzoyl and $R^4$ is methyl.

20. The compound as defined in claim 1 wherein $R^1$ is N-(n-dodecanoyl)-4-amino-3,5-diodobenzoyl and $R^4$ is methyl.

21. The compound as defined in claim 1 wherein $R^1$ is N-(n-dodecanoyl)-p-aminophenylacetyl and $R^4$ is methyl.

22. The compound as defined in claim 1 wherein $R^1$ is N-(n-dodecanoyl)-p-aminocinnamoyl and $R^4$ is methyl.

23. The compound as defined in claim 1 wherein $R^1$ is N-(n-dodecanoyl)-p-aminohippuryl and $R^4$ is methyl.

24. The compound as defined in claim 1 wherein $R^1$ is N-(n-dodecanoyl)-2-aminonicotinyl and $R^4$ is methyl.

25. The compound as defined in claim 1 wherein $R^1$ is N-(n-dodecanoyl)phenylalanyl and $R^4$ is methyl.

* * * * *